(12) United States Patent
Enrooth et al.

(10) Patent No.: US 8,452,405 B2
(45) Date of Patent: May 28, 2013

(54) METHODS AND SYSTEMS FOR MITIGATING THE OCCURRENCE OF ARRHYTHMIA DURING ATRIAL PACING

(75) Inventors: Eric Enrooth, Lino Lakes, MN (US); Yanting Dong, Shoreview, MN (US); Kenneth N. Hayes, Blaine, MN (US); Gary T. Seim, Minneapolis, MN (US); Kevin John Stalsberg, White Bear Lake, MN (US); Aaron McCabe, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 240 days.

(21) Appl. No.: 12/772,725

(22) Filed: May 3, 2010

(65) Prior Publication Data

US 2010/0286743 A1 Nov. 11, 2010

Related U.S. Application Data

(60) Provisional application No. 61/175,709, filed on May 5, 2009.

(51) Int. Cl.
*A61N 1/362* (2006.01)

(52) U.S. Cl.
USPC .................................. 607/28; 607/9

(58) Field of Classification Search
USPC .......................... 607/9, 14, 27–28
See application file for complete search history.

(56) References Cited

U.S. PATENT DOCUMENTS

| | | | |
|---|---|---|---|
| 4,505,276 A | 3/1985 | Markowitz et al. | |
| 4,543,963 A | 10/1985 | Gessman | |
| 4,569,350 A | 2/1986 | Mumford et al. | |
| 5,000,189 A | 3/1991 | Throne et al. | |
| 5,139,028 A | 8/1992 | Steinhaus et al. | |
| 5,217,021 A | 6/1993 | Steinhaus et al. | |
| 5,253,644 A | 10/1993 | Elmvist | |
| 5,273,035 A | 12/1993 | Markowitz et al. | |
| 5,312,450 A | 5/1994 | Markowitz | |
| 5,350,410 A | 9/1994 | Kleks et al. | |
| 5,374,280 A | 12/1994 | den Dulk | |
| 5,383,910 A | 1/1995 | Den Dulk | |

(Continued)

FOREIGN PATENT DOCUMENTS

| EP | 1116494 | 7/2001 |
|---|---|---|
| WO | WO2006065707 | 6/2006 |

OTHER PUBLICATIONS

International Search Report and Written Opinion dated Aug. 26, 2010 from PCT application No. PCT/US2010/033566, 15 pages.

File history for U.S. Appl. No. 11/601,217.

(Continued)

*Primary Examiner* — Rex R Holmes
(74) *Attorney, Agent, or Firm* — Seager, Tufte & Wickhem, LLC

(57) ABSTRACT

Noncaptured atrial paces can result in long-short cardiac cycles which are proarrhythmic for ventricular tachyarrhythmia. Approaches are described which are directed to avoiding proarrhythmic long-short cycles. For cardiac cycles in which the atrial pace captures the atrium, a first post ventricular refractory period (PVARP) and a first A-A interval are used. For cardiac cycles in which the atrial pace does not capture the atrium, both an extended PVARP and an extended A-A interval are used. The A-A interval following a noncaptured atrial pace is extended from an atrial depolarization sensed during the extended PVARP.

12 Claims, 14 Drawing Sheets

U.S. PATENT DOCUMENTS

| | | | |
|---|---|---|---|
| 5,447,519 | A | 9/1995 | Peterson |
| 5,458,623 | A | 10/1995 | Lu et al. |
| 5,476,482 | A | 12/1995 | Lu |
| 5,534,017 | A | 7/1996 | van Krieken et al. |
| 5,549,648 | A | 8/1996 | Stoop |
| 5,601,615 | A | 2/1997 | Markowitz et al. |
| 5,653,738 | A | 8/1997 | Sholder |
| 5,683,431 | A | 11/1997 | Wang |
| 5,713,933 | A | 2/1998 | Condie et al. |
| 5,766,229 | A | 6/1998 | Bornzin |
| 5,779,645 | A | 7/1998 | Olson et al. |
| 5,817,027 | A | 10/1998 | Arand et al. |
| 5,843,137 | A | 12/1998 | Condie et al. |
| 5,857,977 | A | 1/1999 | Caswell et al. |
| 5,871,509 | A | 2/1999 | Noren |
| 5,954,754 | A | 9/1999 | Stoop et al. |
| 6,038,474 | A | 3/2000 | Zhu et al. |
| 6,052,620 | A | 4/2000 | Gillberg et al. |
| 6,076,014 | A | 6/2000 | Alt |
| 6,101,416 | A | 8/2000 | Sloman |
| 6,112,119 | A | 8/2000 | Schuelke et al. |
| 6,128,535 | A | 10/2000 | Maarse |
| 6,163,724 | A | 12/2000 | Hemming et al. |
| 6,167,307 | A | 12/2000 | Hess |
| 6,175,766 | B1 | 1/2001 | Bornzin et al. |
| 6,221,011 | B1 | 4/2001 | Bardy |
| 6,259,950 | B1 | 7/2001 | Mann et al. |
| 6,263,244 | B1 | 7/2001 | Mann et al. |
| 6,270,457 | B1 | 8/2001 | Bardy |
| 6,275,731 | B1 | 8/2001 | Zhu et al. |
| 6,277,072 | B1 | 8/2001 | Bardy |
| 6,280,380 | B1 | 8/2001 | Bardy |
| 6,285,908 | B1 | 9/2001 | Mann et al. |
| 6,312,378 | B1 | 11/2001 | Bardy |
| 6,336,903 | B1 | 1/2002 | Bardy |
| 6,358,203 | B2 | 3/2002 | Bardy |
| 6,363,281 | B1 | 3/2002 | Zhu et al. |
| 6,368,284 | B1 | 4/2002 | Bardy |
| 6,389,316 | B1 | 5/2002 | Bornzin et al. |
| 6,398,728 | B1 | 6/2002 | Bardy |
| 6,408,210 | B1 | 6/2002 | Bornzin et al. |
| 6,418,343 | B1 | 7/2002 | Zhang et al. |
| 6,440,066 | B1 | 8/2002 | Bardy |
| 6,449,503 | B1 | 9/2002 | Hsu |
| 6,456,881 | B1 | 9/2002 | Bornzin et al. |
| 6,473,649 | B1 | 10/2002 | Gryzwa et al. |
| 6,496,730 | B1 | 12/2002 | Kleckner et al. |
| 6,498,949 | B2 | 12/2002 | Levine et al. |
| 6,505,070 | B1 | 1/2003 | Backers |
| 6,505,071 | B1 | 1/2003 | Zhu et al. |
| 6,587,723 | B1 | 7/2003 | Sloman et al. |
| 6,609,028 | B2 | 8/2003 | Struble |
| 6,611,714 | B1 | 8/2003 | Mo |
| 6,618,622 | B1 | 9/2003 | Mann et al. |
| 6,625,489 | B2 | 9/2003 | Sheth et al. |
| 6,643,549 | B1 | 11/2003 | Bradley et al. |
| 6,684,100 | B1 | 1/2004 | Sweeney et al. |
| 6,697,673 | B1 | 2/2004 | Lu |
| 6,721,601 | B1 | 4/2004 | Bornzin et al. |
| 6,768,924 | B2 | 7/2004 | Ding et al. |
| 6,925,326 | B1 | 8/2005 | Levine et al. |
| 6,950,704 | B1 | 9/2005 | Bradley |
| 7,006,869 | B2 | 2/2006 | Bradley |
| 7,076,290 | B2 | 7/2006 | Sheth et al. |
| 7,076,297 | B2 | 7/2006 | Limousin et al. |
| 7,123,954 | B2 | 10/2006 | Narayan et al. |
| 7,130,685 | B2 | 10/2006 | Casavant et al. |
| 7,130,690 | B2 | 10/2006 | Rueter et al. |
| 7,133,718 | B2 | 11/2006 | Bakken et al. |
| 7,177,685 | B2 | 2/2007 | Lincoln et al. |
| 7,319,900 | B2 | 1/2008 | Kim et al. |
| 7,324,848 | B1 | 1/2008 | Turcott |
| 7,330,761 | B2 | 2/2008 | Zhang |
| 7,457,666 | B2 | 11/2008 | Bohn et al. |
| 7,509,168 | B1 | 3/2009 | Mengotto et al. |
| 2005/0131477 | A1 | 6/2005 | Meyer et al. |
| 2005/0131478 | A1 | 6/2005 | Kim et al. |
| 2006/0129197 | A1 | 6/2006 | Zhang et al. |
| 2006/0129199 | A1 | 6/2006 | Zhang et al. |
| 2006/0247693 | A1 | 11/2006 | Dong et al. |
| 2008/0119902 | A1 | 5/2008 | Bohn et al. |
| 2008/0119905 | A1* | 5/2008 | Bohn et al. .................. 607/28 |

OTHER PUBLICATIONS

Restriction Response dated Apr. 12, 2010 from U.S. Appl. No. 11/601,217, 8 pages.

Restriction dated Mar. 12, 2010 from U.S. Appl. No. 11/601,217, 6 pages.

Reply Brief dated May 5, 2009 from U.S. Appl. No. 11/012,692, 9 pages.

Examiner's Answer dated Mar. 12, 2009 from U.S. Appl. No. 11/012,692, 12 pages.

Appeal Brief dated Dec. 8, 2008 from U.S. Appl. No. 11/012,692, 25 pages.

Office Action dated Aug. 25, 2008 from U.S. Appl. No. 11/012,692, 8 pages.

Office Action Response dated Jun. 2, 2008 from U.S. Appl. No. 11/012,692, 8 pages.

Office Action dated Dec. 3, 2007 from U.S. Appl. No. 11/012,692, 6 pages.

Office Action Response dated Sep. 24, 2007 from U.S. Appl. No. 11/012,692, 6 pages.

Office Action dated Aug. 22, 2007 from U.S. Appl. No. 11/012,692, 6 pages.

International Search Report and Written Opinion dated Apr. 15, 2008 from PCT Application No. PCT/US2007/023820, 13 pages.

International Preliminary Report on Patentability dated May 28, 2009 from PCT Application No. PCT/US2007/023820, 5 pages.

* cited by examiner

METHODS AND SYSTEMS FOR MITIGATING THE OCCURRENCE OF ARRHYTHMIA DURING ATRIAL PACING

RELATED APPLICATIONS

This application claims the benefit of Provisional Patent Application Ser. No. 61/175,709, filed on May 5, 2009, to which priority is claimed pursuant to 35 U.S.C. §119(e) and which is hereby incorporated herein by reference.

FIELD OF THE INVENTION

The present invention relates generally to implantable medical devices and, more particularly, to atrial capture detection.

BACKGROUND OF THE INVENTION

When functioning normally, the heart produces rhythmic contractions and is capable of efficiently pumping blood throughout the body. However, due to disease or injury, the heart rhythm may become irregular resulting in diminished pumping efficiency.

Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending in, on, or about the patient's heart are connected to electrodes that electrically couple to the heart tissue for sensing the heart's electrical signals and for delivering stimulation pulses to the heart in accordance with various therapies.

Cardiac devices operate to stimulate the heart tissue electrically coupled to the electrodes to produce a contraction of the tissue. Pacemakers deliver a series of low energy pace pulses timed to assist the heart in producing a contractile rhythm that maintains cardiac pumping efficiency. Pace pulses may be intermittent or continuous, depending on the needs of the patient. There exist a number of categories of cardiac devices that provide pacing pulses, with various modes for sensing and pacing one or more heart chambers.

When a pace pulse produces a contraction in the heart tissue, the electrical cardiac signal following the contraction is denoted the evoked response signal. Superimposed on the evoked response signal is a signal associated with residual post pace polarization at the electrode-tissue interface. The magnitude of the residual post pace polarization signal, or pacing artifact, may be affected by a variety of factors including the electrodes used for pacing, the polarization of the electrodes, lead impedance, patient impedance, pace pulse width, and pace pulse amplitude, for example. The post pace polarization signal is present whether or not the pace captures the heart tissue.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold may be required for efficient pace energy management. If the pace pulse energy is too low, the pace pulses may not reliably produce a contractile response in the heart and may result in ineffective pacing. If the pace pulse energy is too high, the patient may experience discomfort and/or the battery life of the device will be shorter.

Capture detection allows the cardiac device to adjust the energy level of pace pulses to correspond to the optimum energy expenditure that reliably produces a contraction. Further, capture detection allows the cardiac device to initiate a back-up pulse at a higher energy level whenever a pace pulse does not produce a contraction.

SUMMARY

Embodiments of the present invention are directed to methods and systems to mitigate tachyarrhythmia which can be promoted by non-captured atrial beats.

Embodiments of the invention involve methods of operating an implantable cardiac device to deliver pacing to an atrium. For cardiac cycles in which the atrial pace captures the atrium, a post ventricular atrial refractory period (PVARP) first PVARP duration and an A-A interval having a first A-A interval duration are used. For cardiac cycles in which the atrial pace does not capture the atrium, both a PVARP having second duration and an A-A interval having a second duration are used, wherein the second PVARP duration is greater than the first PVARP duration and the second A-A interval duration is greater than the first A-A interval duration.

For example, the A-A interval following a noncaptured atrial pace may be extended from an atrial depolarization sensed during the second PVARP. The second PVARP may be have a duration of about 500 ms. The second A-A interval duration may be about 300 ms beyond the atrial depolarization sensed during the second PVARP.

In some implementations the atrial pacing is delivered during an atrial capture threshold test. A rate stabilization atrial pace is delivered after expiration of the second A-A interval, the rate stabilization pace initiating a next cardiac cycle and having an energy selected to produce capture of the atrium. For example, the atrial capture threshold test may involve a step-down capture threshold test. In response to a final noncaptured stepped down test pace, the capture threshold test is ended after the rate stabilization pace. During the atrial capture threshold test, a set of test pacing parameters may be substituted in place of normal pacing parameters. In this scenario, ending the capture threshold test involves returning to the normal pacing parameters after delivery of the rate stabilization pace, e.g., on a next beat after ending the capture threshold test.

Embodiments of the invention are directed to an implantable cardiac therapy device configured to deliver pacing pulses to an atrium. The device includes electrodes configured to be electrically coupled to an atrium. A pulse generator delivers pacing pulses to the atrium via the electrodes. A cardiac response classification processor discriminates non-captured responses to the pacing pulses from other cardiac responses. A pacing control module controls delivery of the atrial pacing pulses and timing intervals used during pacing cycles, including using a post ventricular atrial refractory period (PVARP) having a first PVARP duration and an A-A interval having a first A-A interval duration for cardiac cycles in which an atrial pace captures the atrium, and using both a PVARP having a second duration and an A-A interval having a second duration during cardiac cycles in which the atrial pace does not capture the atrium, wherein the second PVARP duration is greater than the first PVARP duration and the second A-A interval duration is greater than the first A-A interval duration.

Another approach involves operating a cardiac device to deliver atrial and ventricular pacing. An atrial pace is delivered to the atrium during a cardiac cycle and a ventricular pace is scheduled to occur during the cardiac cycle after an atrioventricular (AV) delay. The device senses for a cardiac response to the atrial pace during an evoked response interval that follows delivery of the atrial pace. The device determines if the cardiac response is noncapture based on the sensing during the evoked response interval. In response to determining that the cardiac response to the atrial pace is noncapture, the cardiac device implements the following steps: delivers an atrial backup pace having an energy sufficient to effect capture of the atrium, cancels the scheduled ventricular pace, extends the AV delay or initiates a second AV delay, and delivers a ventricular pace after the extended AV delay or the second AV delay.

In response to determining that the cardiac response to the atrial pace is not noncapture based on the sensing during the evoked response interval, the device continues to sense for the cardiac response to the atrial pace during a second evoked response interval. The device may determine that the cardiac response is capture, fusion, or another cardiac response based on the sensing during the second evoked response interval.

Another approach for operating a cardiac device involves delivering an atrial pace to the atrium during a cardiac cycle and scheduling a ventricular pace to occur during the cardiac cycle after an atrioventricular (AV) delay. The device senses for a cardiac response to the atrial pace during an evoked response interval that follows delivery of the atrial pace and determines that the cardiac response is not noncapture based on the sensing during the evoked response interval. In response to determining that the cardiac response to the atrial pace is not noncapture, the device implements the following steps: delivers an atrial backup pace having an energy sufficient to effect capture of the atrium, cancels the scheduled ventricular pace; decreases the AV delay, and delivers a ventricular pace after the decreased AV delay.

The above summary is not intended to describe each embodiment or every implementation of the present invention. Advantages and attainments, together with a more complete understanding of the invention, will become apparent and appreciated by referring to the following detailed description and claims in conjunction with the accompanying drawings.

Figure 1:
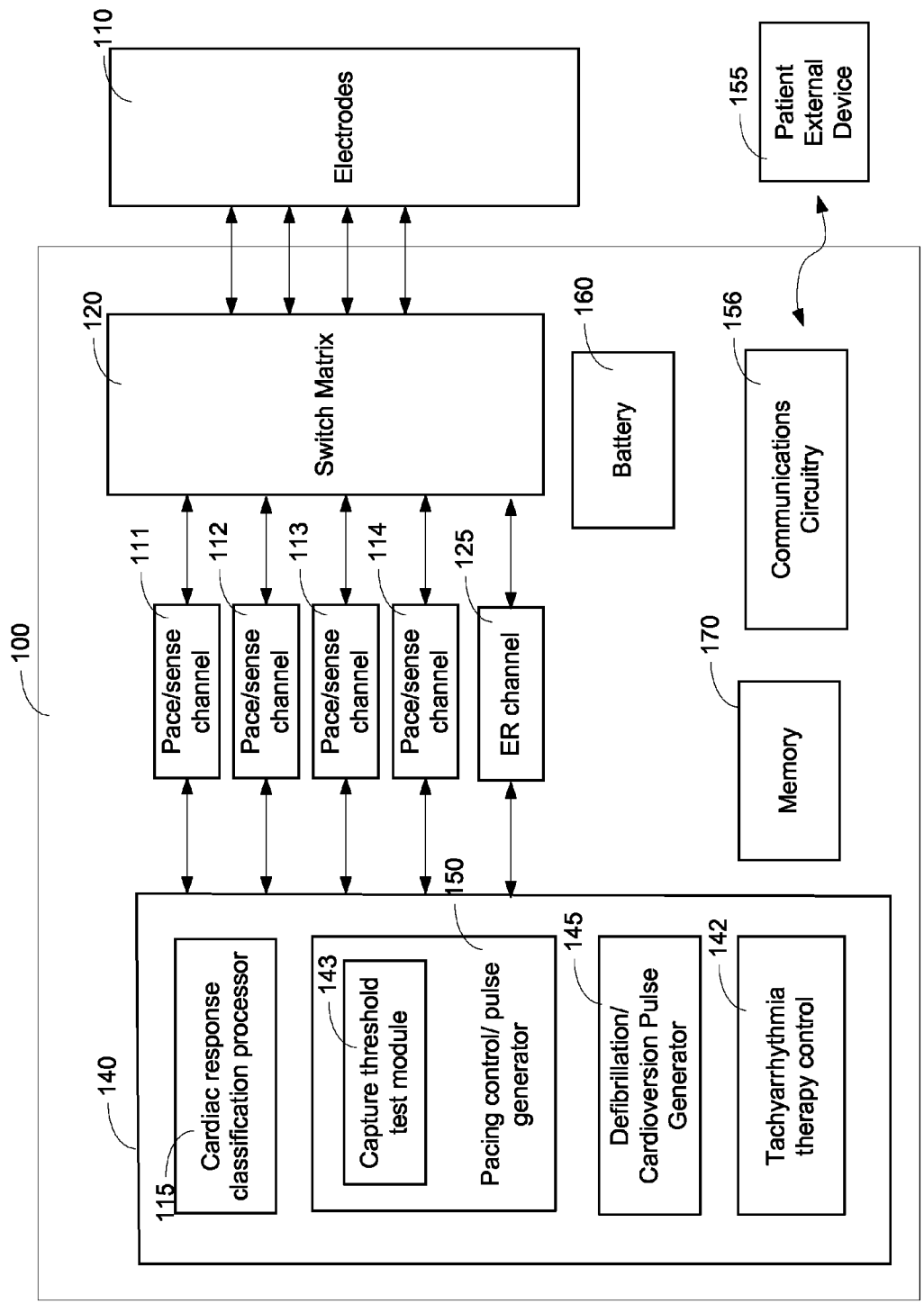
FIG. 1 is a block diagram of a cardiac device configured to perform cardiac pacing and/or capture threshold testing while mitigating the occurrence of tachyarrhythmia following one or more non-captured beats in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown, by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-captured beat. Non-capture may occur, for example, if the pacing pulse energy is too low, and/or if the pacing pulse is delivered during a refractory period of the cardiac tissue.

The cardiac pacing response may be determined using a variety of approaches. For example, the cardiac signal sensed following a pacing pulse may be evaluated to discriminate between various pacing responses, e.g., noncapture, capture, fusion, pseudofusion, pseudopseudofusion, noncapture with intrinsic activation. The amplitude of the sensed atrial signal during an evoked response interval (ERI) following an atrial pacing pulse may be used to rule out non-capture from other pacing responses, e.g., capture, fusion, pseudofusion, pseudopseudofusion, or non-capture with intrinsic activation. If the amplitude of the cardiac signal within the ERI is less than (or greater than, depending on signal orientation) a threshold level, then non-capture is detected by the device. In other approaches, the presence of retrograde conduction from the ventricle to the atrium may be used to indicate non-capture of the atrium as described in commonly owned U.S. Pat. No. 7,587,240 which is incorporated herein by reference.

If a pacing pulse does not capture the atrium, an atrial depolarization caused by retrograde conduction to the atrium from an intrinsic or paced ventricular depolarization (retrograde P-wave), or by an intrinsic atrial depolarization (intrinsic P-wave), may lead to noncapture on the next pacing cycle. Noncapture occurs on the next pacing cycle because the atrial tissue remains refractory due to the occurrence of the retrograde or intrinsic P-wave. In a capture threshold test, for example, this detection of non-capture could be misleading because the non-capture is caused by tissue refractoriness, not the level of the pacing voltage. In addition, if tracked, the retrograde or intrinsic P-wave may also cause undesirable fast pacing, denoted pacemaker mediated tachyarrhythmia (PMT). Furthermore, a tracked retrograde or intrinsic P-wave which follows a non-captured pacing cycle can lead to a series of long-short timing cycles. Long-short cycles are proarrhythmic for ventricular tachyarrhythmia. Thus, it is desirable to implement processes that avoid proarrhythmic pacing cycles following non-captured atrial beats. In particular, it is desirable to avoid proarrhythmic pacing cycles during atrial capture threshold testing which relies on the occurrence of non-captured atrial beats to determine the atrial capture threshold.

Prior approaches involved pacing protocols designed to reduce retrograde conduction or processes for reducing pacemaker mediated tachyarrhythmia following non-captured paces. However, these processes could be insufficient to prevent proarrhythmic long-short cycles after a non-captured atrial pace. Prior methods used could potentially cause or exacerbate the proarrhythmic cycles. Thus, the present invention addresses the problem of proarrhythmic long-short cycles which may occur during capture threshold testing and/or during non-threshold test pacing. These processes may be implemented in addition to processes designed to avoid pacemaker mediated tachyarrhythmia or to avoid retrograde conduction. The examples provided herein may be used in conjunction with atrial capture threshold testing and/or non-threshold test pacing. For purposes of illustration, in most examples, the processes are described as occurring during a capture threshold test. It will be appreciated that the approaches to avoid pacemaker mediated tachyarrhythmia and/or to avoid retrograde conduction may also advantageously be used during non-threshold test pacing.

In one example of an automatic capture threshold procedure, the pacemaker delivers a sequence of pacing pulses to the heart and detects the cardiac pacing responses to the pace pulses. In a step down capture threshold test, the energy of the pacing pulses may be decreased in discrete steps until a predetermined number of non-capture responses occur to confirm the capture threshold and/or to provide a rate stabilization period prior to ending the capture threshold test. For example, if a predetermined number of non-capture responses occur, e.g., x out of y non-capture responses or a predetermined number of non-capture responses at a particular pacing energy, then loss of capture (LOC) is confirmed. The pacing energy used prior to the LOC condition is identified as the capture threshold. After the capture threshold is initially identified, the pacemaker may increase the stimulation energy in discrete steps until a predetermined number of capture responses occur to confirm the capture threshold. Other procedures for implementing capture threshold testing may be utilized. In one example, the pacing energy may be increased in discrete steps until capture is detected. In another example, the pacing energy may be adjusted according to a binomial search pattern, or other search patterns.

FIG. 1 shows a block diagram of a cardiac pacing system that may be used to perform a capture threshold test and to deliver non-threshold test pacing, including adjusting one or more intervals used in pacing to avoid proarrhythmic pacing cycles in accordance with the approaches of the present invention. The cardiac pacing system in FIG. 1 includes an implantable cardiac device (ICD) 100 such as a device incorporating the functions of a pacemaker, pacemaker/defibrillator, or cardiac resynchronization therapy (CRT) device, enclosed within a housing and coupled to cardiac electrodes 110.

The cardiac electrodes 110 are used to detect electrical signals produced by the heart and to provide electrical energy to the heart. The electrodes 110 may include electrodes used for pacing, sensing, and/or cardioversion/defibrillation. For example, any of the electrodes 110 may be disposed to sense electrical activity primarily from the right ventricle, left ventricle, right atrium, or left atrium. One or more electrodes 110 may be disposed to sense global electrical activity which comprises a superposition of a number of cardiac electrical signals from multiple chambers. The housing and/or header of the ICD 100 may incorporate one or more can and/or indifferent electrodes used to provide electrical stimulation energy to the heart and/or to sense cardiac electrical activity. The electrodes 110 can be selectively coupled though a switch matrix 120 to any of the pace/sense channels 111-114 or the evoked response channel 125 of the ICD 100.

As illustrated in FIG. 1, the ICD 100 may include one or multiple channels 111-114 for pacing and/or sensing one or more heart chambers. For example, through the pace/sense channels 111-114, the ICD may pace and/or sense the left atrium through a pace sense channel 111; may pace and/or sense the right atrium through a pace/sense channel 112; may pace and/or sense the left ventricle through a pace/sense channel 113; and may pace and/or sense the right ventricle through a pace/sense channel 114. The sensing portion of each pace/sense channel may incorporate signal processing circuitry to digitize, amplify, filter, and/or otherwise process the cardiac signal sensed via the electrodes 110. The ICD may include a sense channel 125 configured for detection of the evoked response (ER).

The ICD 100 may include circuitry 140 capable of controlling the delivery of pacing pulses and/or cardioversion/defibrillation shocks to the right ventricle, left ventricle, right atrium and/or left atrium to provide bradyarrhythmia therapy, tachyarrhythmia therapy, and/or cardiac resynchronization therapy, for example. If tachyarrhythmia therapy is provided, the ICD circuitry 140 may include an arrhythmia detector that operates to detect atrial and/or ventricular tachyarrhythmia and/or fibrillation. Under control of the tachyarrhythmia therapy control 142, the defibrillation/cardioversion pulse generator 145 is capable of generating high energy shocks to terminate the detected tachyarrhythmia episodes.

The pacing control/pulse generator 150 is configured to generate and control delivery of pacing pulses for treating bradyarrhythmia, for synchronizing the contractions of contralateral heart chambers using biatrial and/or biventricular pacing, for delivering anti-tachyarrhythmia pacing (ATP), and/or for performing capture threshold tests, such as atrial and/or ventricular capture threshold tests. Pacing stimulation may be delivered to one or more heart chambers during a cardiac cycle. The pacing control 150 includes a number of interval timers for timing various intervals used in delivering pacing therapy and/or capture threshold testing. These intervals may include, for example, pacing escape intervals such as A-A intervals (the pacing interval between two consecutive atrial events), V-V intervals (the pacing interval between two consecutive ventricular events), AV delay (the pacing interval between an atrial event and a next ventricular pace), and refractory periods, such as the post ventricular atrial refractory period (PVARP) which alters sensing functions in the atrium following ventricular paces and/or senses. For example, during a refractory period, a sensed event may not trigger the same pacing behavior as a sensed event outside the refractory period. PVARP is one example of a refractory period, however, various pacing protocols implemented by the ICD 100 may use various types of refractory periods to alter the response to sensed events. For example, the ICD 100 may implement refractory periods during fast atrial rhythms as part of an atrial flutter response (AFR). The refractory periods of atrial flutter response and their effect on pacing with capture detection according to embodiments of the invention are further described with reference to FIGS. 5B and 5C.

The pacing control 150 may implement various pacing algorithms at selected times to provide pacing that mimics or more closely resembles physiological cardiac responses. For example, the pacing control 150 may implement algorithms to provide rate adaptive pacing based on the patient's activity level and/or metabolic demand; and/or may provide rate smoothing to avoid abrupt changes in pacing rate; and/or may provide mode switching to avoid accelerated ventricular pacing during fast atrial rates; and/or may implement algorithms that promote intrinsic or paced beats, and/or may implement other pacing protocols depending on the therapeutic needs of the patient.

The pacing control 150 includes a capture threshold test module 143 that controls the operation of pacing during capture threshold testing. For example, the capture threshold test module 143 may control the operation of an automatic step down threshold test for an atrium. The pacing control 150 may set output voltages for pacing pulses, schedule pacing pulses or cancel scheduled pacing pulses, initiate, terminate or modify pacing intervals or refractory periods.

The ICD 100 includes a pacing response classification (PRC) processor 115. In some embodiments, the PRC processor 115 is coupled to the ER channel 125 and is configured to use the ER channel signal to discriminate between various responses to pacing, such as capture, noncapture with or without intrinsic activation, fusion, pseudofusion, pseudopseudofusion, etc. Pacing response classification may be implemented by the PRC processor 115 for capture threshold testing and/or capture verification during therapeutic pacing. The PRC processor 115 may be configured to acquire and/or use various thresholds, intervals, and/or morphological templates in the analysis of signals that follow a pacing pulse to determine the cardiac response to the pacing pulse. Discrimination between various possible pacing responses can be performed by the PRC processor 115 based on comparison of a cardiac signal sensed following the pacing pulse to one or more intervals, thresholds, or morphology templates, for example.

The ICD 100 is typically powered by an electrochemical battery 160. A memory 170 stores data and program commands used to implement various therapeutic and/or diagnostic functions of the ICD. Data and program commands may be transferred between the ICD 100 and a patient-external device 155 via telemetry-based communications circuitry 156.

FIG. 1 shows a medical system, including an ICD 100, cardiac electrodes 110, and a patient external device 155, divided into functional blocks. It is understood by those skilled in the art that there exist many possible configurations in which these functional blocks can be arranged. The example depicted in FIG. 1 is one possible functional arrangement. Other arrangements are also possible. For example, more, fewer or different functional blocks may be used to describe a medical system suitable for implementing the processes of the present invention. In addition, although the ICD 100 depicted in FIG. 1 contemplates the use of programmable microprocessor-based logic circuitry, other types of circuit implementations may be utilized.

Figure 2A:
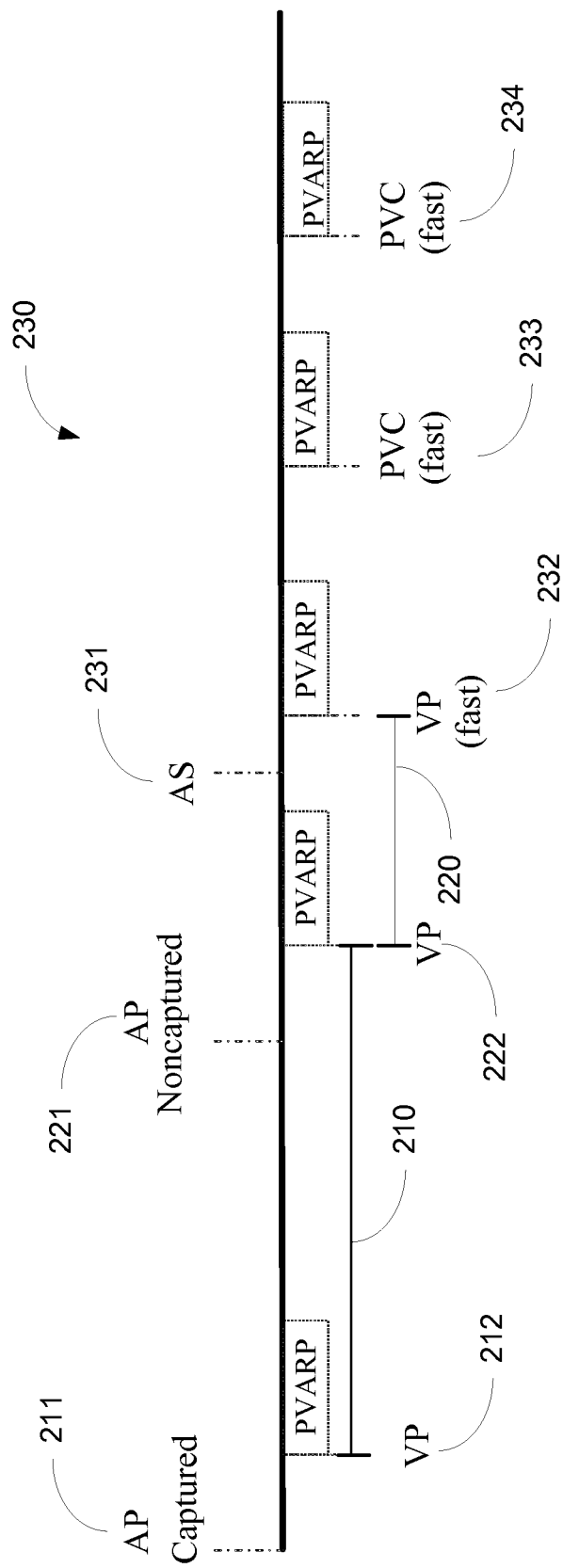
FIG. 2A is a timing diagram illustrating several cardiac cycles of a capture threshold test during which a spontaneous tachyarrhythmia is induced by a proarrhythmic long-short timing sequence.
Figure 2B:
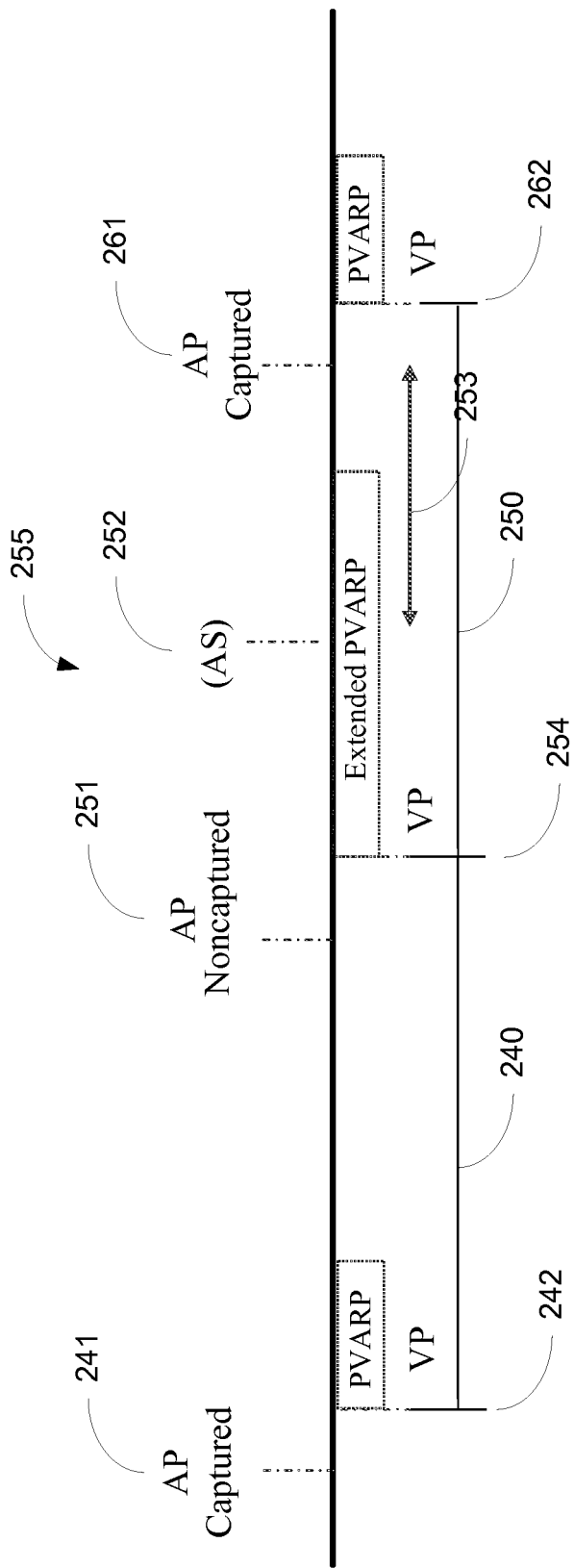
FIG. 2B is a timing diagram illustrating a capture threshold test that includes timing sequences to avoid proarrhythmic cycles in accordance with embodiments of the invention.

Embodiments of the invention are directed to various approaches to mitigate the occurrence of arrhythmias following non-captured beats that occur during atrial pacing, including during atrial capture threshold testing. FIGS. 2A and 2B illustrate how one approach can be used to mitigate arrhythmias. The initiation of a ventricular tachyarrhythmia is illustrated in the timing diagram of FIG. 2A. A first atrial pace 211 is delivered, which is captured, and a ventricular pace 212 is delivered after an AV delay. A PVARP occurs after the ventricular pace 212. The next atrial pace 221 does not capture the atrium. A ventricular pace 222 is delivered after an AV delay and a PVARP is initiated after the ventricular pace 222. An atrial depolarization 231 occurs after the PVARP. The atrial depolarization 231 may occur either because the atrium spontaneously depolarizes or because the ventricular pace 222 retrogradely conducts to the atrium. Both of these scenarios are possible because the atrial tissue is not refractory following the non-captured atrial pace 221. The atrial depolarization 231 is tracked, thus an AV delay is initiated which is followed by a ventricular pace 232.

As illustrated in FIG. 2A, the first and second ventricular intervals 210, 220 produce a long-short timing sequence which is proarrhythmic. A ventricular tachyarrhythmia 230 is initiated following the long-short cycles 210, 220 resulting in a number of fast ventricular depolarizations 233, 234. The initiation of the ventricular tachyarrhythmia 230 is undesirable and, if sustained, has the possibility of accelerating to ventricular fibrillation.

FIG. 2B is a pacing timing diagram illustrating an approach that avoids the proarrhythmic long-short cycles illustrated in FIG. 2A. A first atrial pace 241 is delivered which is captured, and a ventricular pace 242 is delivered following an AV delay. The ventricular pace 242 initiates a PVARP, e.g. a PVARP of about 250 ms. The next atrial pace 251 does not produce capture. A ventricular pace 254 is delivered following an AV delay and initiates an extended PVARP that is longer than the PVARP used following the captured atrial pace 241. For example, the extended PVARP may have a value of about 500 ms.

An intrinsic or retrograde P-wave 252 may occur during the extended PVARP, as illustrated in FIG. 2B. Because this P-wave 252 occurs within PVARP (denoted a refractory sensed P-wave), it is not tracked and does not initiate an AV delay. In addition, to promote capture of the next atrial pace 261, the atrial pace following the refractory sensed P-wave 252 is delayed from the refractory sensed P-wave 252 by an interval 253 that exceeds the tissue refractory period for the atrium, e.g., about 300 ms. Implementation of the delay interval 253 allows the atrial tissue to recover and become nonrefractory following the retrograde P-wave before the next atrial pace 261 is delivered. The atrial pace 261 is captured, and following an AV delay, the next ventricular pace is delivered 262.

As can be appreciated from observing the ventricular intervals 240, 250 of FIG. 2B, the pacing protocol described, including both extending the PVARP following the non-captured atrial pace 251 and delaying the next atrial pace 261 by an interval 253 in the atrial pacing cycle 255 that starts with a non-captured atrial beat 251, avoids the potential proarrhythmic long-short intervals illustrated in FIG. 2A. Cardiac cycles including both an extended PVARP and the atrial pace delay 253 may be used for non-captured cardiac cycles, e.g., each non-captured cardiac cycle of a capture threshold test.

Figure 3:
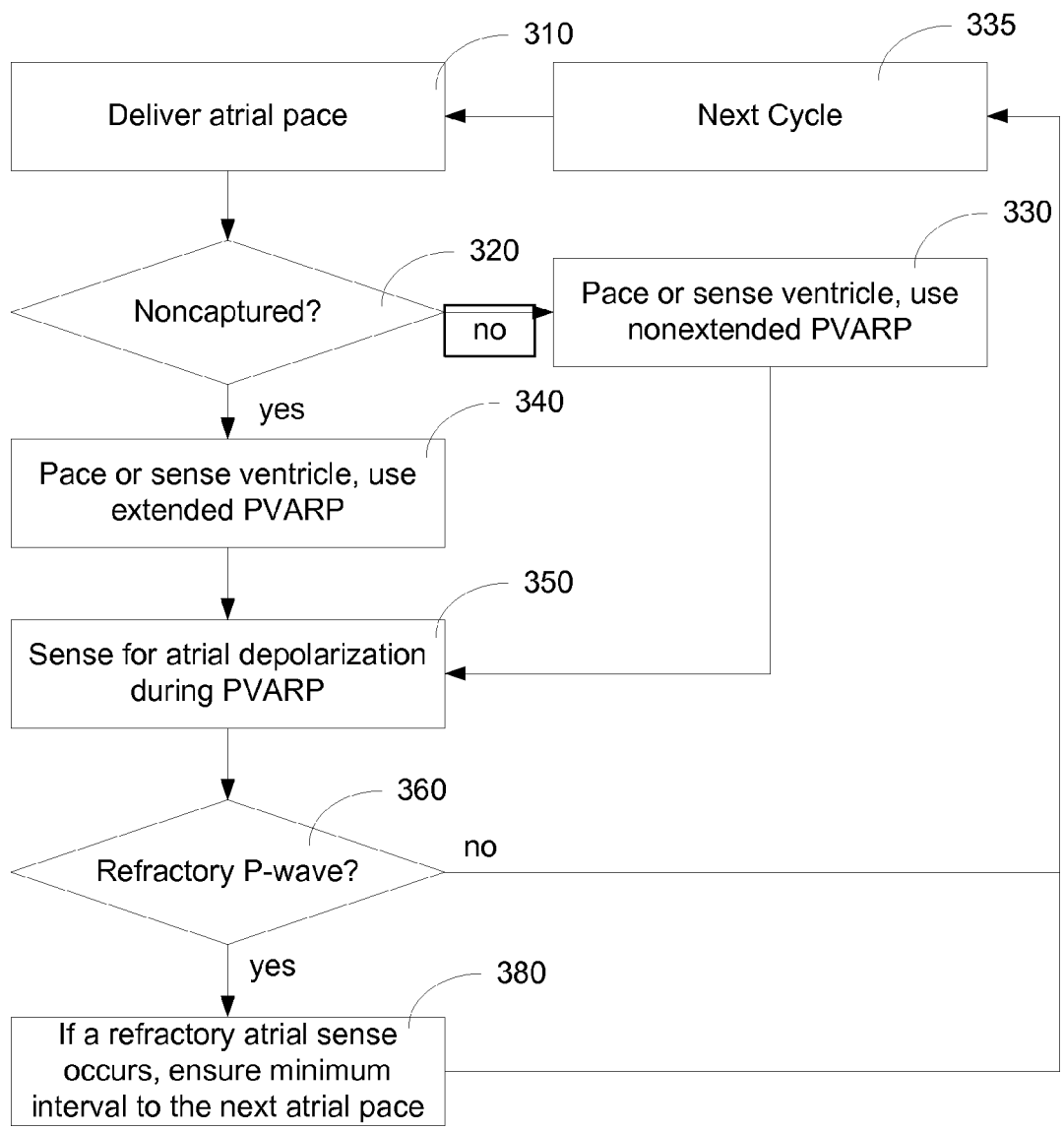
FIG. 3 is a flow diagram illustrating a process of avoiding proarrhythmic cycles by extending the PVARP and the A-A interval of a noncaptured cardiac cycle in accordance with embodiments of the invention.

The flow diagram of FIG. 3 describes the method of operating a pacemaker to mitigate the occurrence of arrhythmia during capture threshold testing and non-threshold test pacing. The process of FIG. 3 employs the approach illustrated by the timing diagram of FIG. 2B. A cardiac cycle begins with delivery 310 of an atrial pace. The device determines 320 if the atrial pace is non-captured. If the pace is not non-captured, then the ventricle is paced 330 during the cardiac cycle unless the scheduled ventricular pace is inhibited by a ventricular sense. The ventricular pace or sense is followed by a non-extended PVARP.

If the atrial pace is non-captured 320, then the ventricular pace or sense for the cardiac cycle is followed 340 by an extended PVARP. During the extended or the non-extended PVARP, the device senses 350 for an atrial depolarization (a refractory P-wave). If the refractory P-wave is not sensed, then the atrial pace that starts the next cardiac cycle 335 is delivered 310 as previously scheduled unless inhibited by an intrinsic atrial depolarization. If the refractory P-wave is sensed 360, then the atrial pace for the next cardiac cycle is delayed 380 for an interval that is selected to ensure that the atrial tissue is not refractory when the next atrial pace is delivered. The refractory P-wave does not initiate an AV delay.

Some embodiments of the invention are directed to an approach for ensuring that atrial paces that occur just prior to the end of a step down atrial capture threshold test, do not produce proarrhythmic cycles. This approach involves delivering one or more rate stabilization paces at the end of the step down portion of the capture threshold test and before the pacing parameters return to a non-test, normal pacing mode. These rate stabilization paces are delivered at an energy sufficient to ensure capture, so that proarrhythmic long-short intervals caused by noncaptured paces are avoided.

Figure 4A:
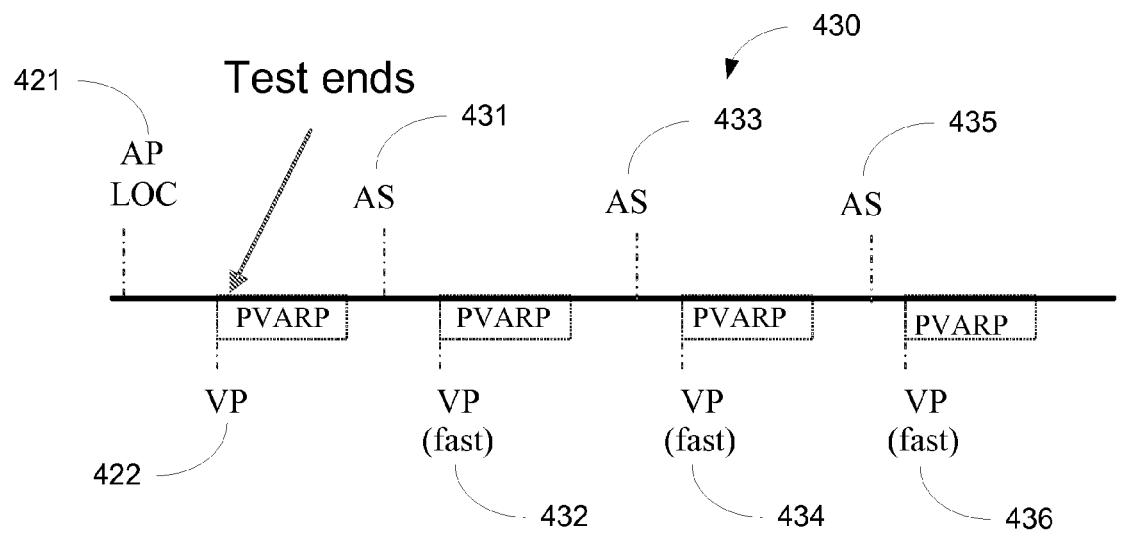
FIG. 4A is a timing diagram that illustrates an end of test for a capture threshold test followed by pacemaker mediated tachyarrhythmia.
Figure 4B:
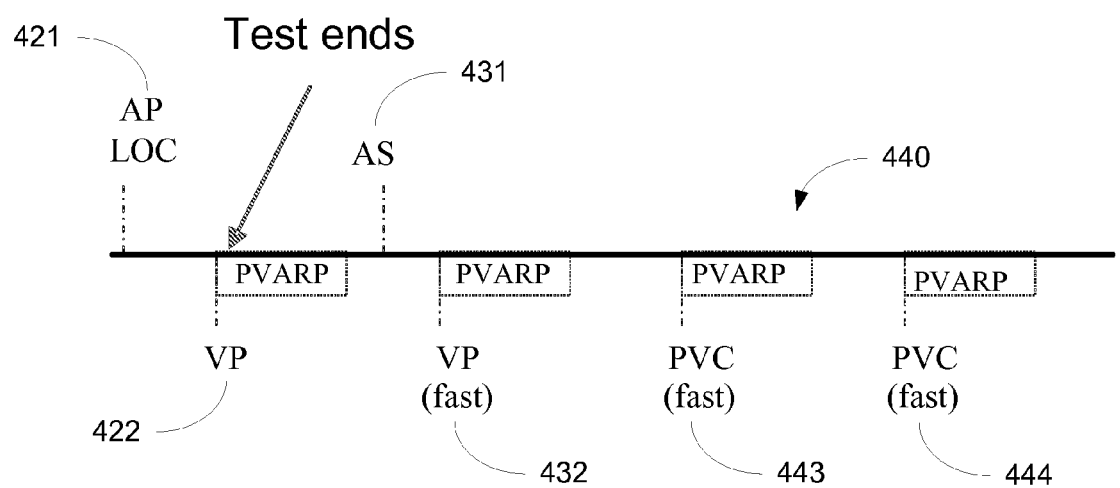
FIG. 4B is a timing diagram illustrating an end of test for a capture threshold test followed a tachyarrhythmia induced by long-short pacing cycles.

The pacing timing diagrams of FIGS. 4A and 4B illustrate a step down atrial capture threshold test that does not use rate stabilization paces. In each scenario, the final atrial pace 421 of the threshold test is non-captured and indicates confirmation of loss of capture (LOC). Confirmation of LOC may occur, for example, if x out of the last y paces are non-captured or if z paces at the same energy level are non-captured. A ventricular pace 422 is delivered after an AV delay. The step down test ends after the ventricular pace 422 that is triggered by the final LOC atrial pace 421. The final ventricular pace 422 of the step down test initiates a PVARP. Because the last atrial pace 421 was not captured, the atrial tissue is left in a non-refractory condition after the end of the step down test. An intrinsic or retrograde P-wave 431 occurs outside the PVARP and is tracked, resulting in a fast ventricular pace 432. In one scenario, shown in FIG. 4A, a PMT is initiated following the end of the step down test as follows: on the cardiac cycle after the fast ventricular pace 432, a retrograde P-wave 433 occurs due to the depolarization caused by the ventricular pace 432 being retrogradely conducted to the atrium. The retrograde P-wave 433 occurs outside of PVARP and is again tracked resulting in another fast ventricular beat 434. The fast ventricular beat 434 is also is retrogradely conducted causing the device to sense another atrial depolarization 435 outside PVARP, which triggers another fast ventricular pace 436, and so on until the PMT is interrupted.

In another scenario, as illustrated in FIG. 4B, ending the step down test with a non-captured atrial pace 421 may cause proarrhythmic long-short pacing cycles initiating a tachyarrhythmia. The intrinsic atrial depolarization or retrogradely conducted P-wave 431 that follows a non-captured atrial pace 421 results in a fast ventricular pace 432 that produces a long-short sequence. The long-short sequence initiates a sequence of premature ventricular contractions 443, 444 of a ventricular tachyarrhythmia 440.

Figure 4C:
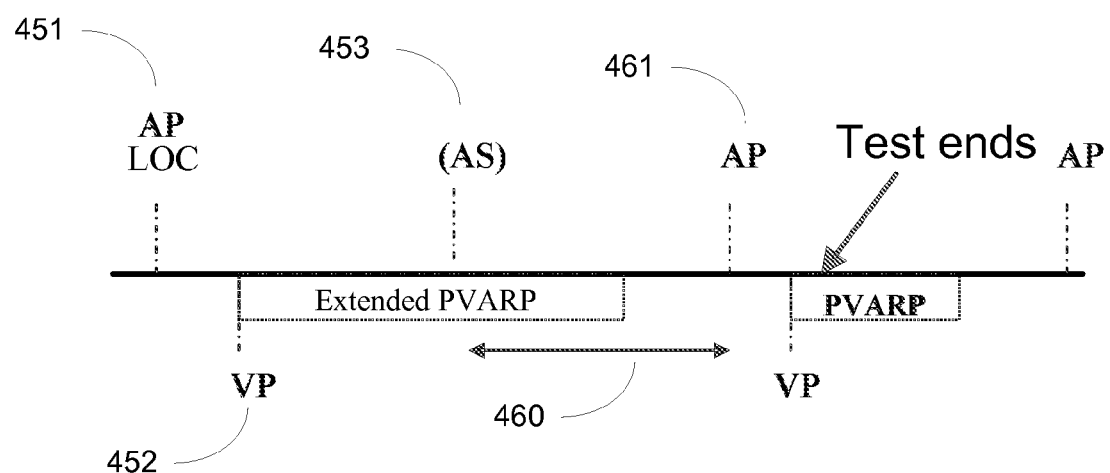
FIG. 4C is a timing diagram illustrating an end of test for a capture threshold test with avoidance of proarrhythmic timing cycles in accordance with embodiments of the invention.

As illustrated in the pacing diagram of FIG. 4C, the likelihood of PMT or initiation of a tachyarrhythmia at the end of the atrial capture threshold test is decreased when the test ends with one or more pacing cycles that include rate stabilization beats, i.e., intrinsic atrial beats and/or captured atrial paces 461, rather than a non-captured atrial pace. In addition to ending the test with at least one pacing cycle including an intrinsic event or captured atrial pace 461, the arrhythmia mitigation techniques described in connection with FIGS. 2B and 3 may also be employed.

FIG. 4C illustrates the use of a rate stabilization pace 461 that is delivered following the last noncaptured atrial pace 451 of the threshold test. After the last noncaptured atrial pace 451, a ventricular pace 452 is delivered or is inhibited by a ventricular sense. The PVARP initiated by the ventricular sense or pace 452 is extended to prevent tracking the refractory retrograde (or spontaneous) P-wave 453. If a refractory P-wave 453 is sensed, then the timing of the next atrial pace 461 is delayed by an interval 460 that exceeds the tissue refractory interval of the atrial tissue. The rate stabilization atrial pace 461 is delivered after the interval 460 at an energy sufficient to produce capture, e.g., 2× the atrial capture threshold. The atrial capture threshold test ends after the rate stabilization cycle.

Figure 5A:
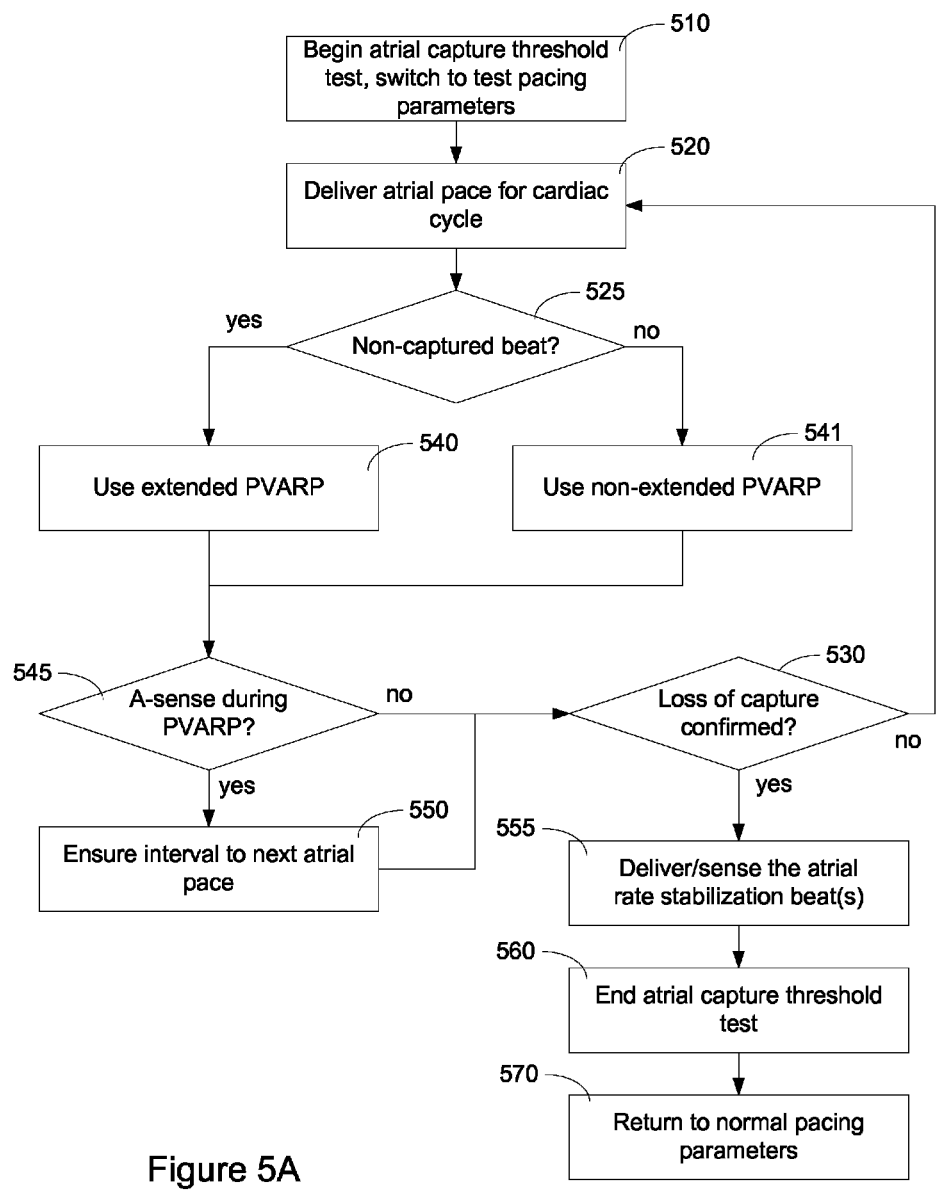
FIG. 5A is flow diagram illustrating a process for ending an atrial capture threshold test in accordance with embodiments of the invention.

The flow diagram of FIG. 5A illustrates a step down atrial capture threshold test including one or more rate stabilization paces. Before the step down portion of the atrial capture threshold test begins, threshold test parameters (e.g., pacing rate, pacing voltage, AV delay, etc.) are substituted 510 for the previous pacing parameters used during the normal pacing protocol. During the capture threshold test, the energy of the delivered atrial paces 520 is incrementally stepped down until loss of capture is confirmed 530. For example, x of y non-captured atrial paces may confirm loss of capture, or z non-captured atrial paces delivered at the same energy level may confirm loss of capture.

If a non-captured atrial beat is detected 525, the PVARP is extended 540 for the cardiac cycle. If the atrial beat is not non-captured 525, then a non-extended PVARP is used for the cardiac cycle. The ICD senses 545 for an atrial depolarization during the PVARP. If the atrial depolarization is detected during the PVARP, the ICD may delay the next atrial pace to ensure 550 an interval of time between the sensed atrial depolarization and the next atrial pace that will allow the atrial tissue to return to a non-refractory condition. If no atrial depolarization is detected 545 during the PVARP, then the next atrial pace is delivered as scheduled, unless inhibited by a non-refractory atrial sense. Note that although the process is described in FIG. 5A as being performed during a capture threshold test, PVARP extension on detection of non-capture and/or delaying the next atrial pace following a refractory sensed atrial event are also applicable during non-capture threshold test therapeutic pacing with capture detection.

The cardiac cycles continue until loss of capture is confirmed 530. When loss of capture is confirmed, then the one or more next atrial cycles 555 are rate stabilization cycles which include a captured atrial pace unless the atrial pace is inhibited by an intrinsic atrial depolarization. If an atrial pace is delivered during the rate stabilization cycle, it is delivered at a pacing energy that exceeds the capture threshold to ensure capture. After the rate stabilization cycles 555, the atrial capture threshold test ends 560. Normal pacing parameters are restored 570 and the non-test pacing protocol resumes.

Figure 5B:
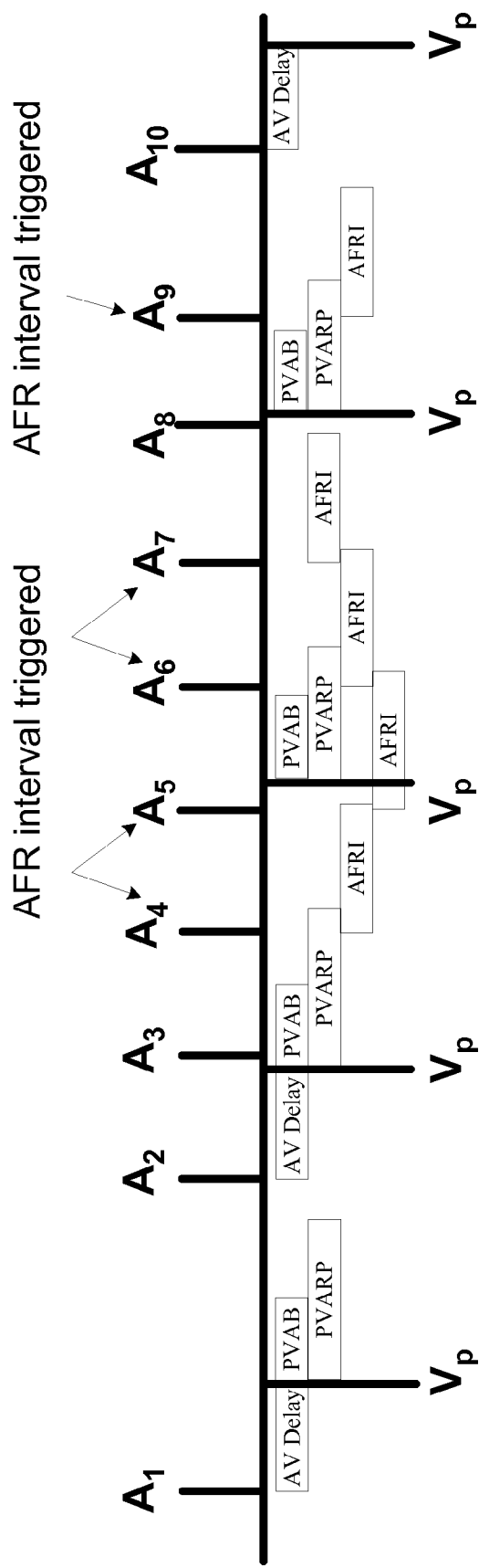
FIG. 5B illustrates the operation of an implantable cardiac device (ICD) implementing atrial flutter response.

In some pacing scenarios the device may use other refractory periods in addition to PVARP. For example, the ICD may respond to detection of fast atrial rhythms by implementing an atrial flutter response (AFR) which involves the use of refractory periods to prevent pacing into the atrial vulnerable period and to prevent tracking fast atrial beats. FIG. 5B illustrates the operation of an AFR that may be implemented by an ICD. In one implementation of an AFR, a detected atrial event within PVARP or within a previously initiated AFR interval (AFRI) will start an AFR interval of a predetermined duration, e.g., about 260 ms. Detection of atrial events inside the AFRI will be classified as refractory events and will not be tracked. Tracking begins again for a cycle that includes an atrial depolarization that occurs after both the AFRI and the PVARP have expired. Paced atrial events scheduled to occur inside an AFRI may be delayed until the AFRI has expired or may be canceled.

FIG. 5B is a timing diagram illustrating the AFR. Atrial events A1 and A2 are sensed events and each of A1 and A2 initiate an AV delay with a ventricular pace, Vp, delivered following the AV delay. Atrial event A3 occurs during a post ventricular atrial blanking period (PVAB) and is not tracked and does not initiate an ATRI. Atrial event A4 occurs during the PVARP initiated by the ventricular pace following A2. Atrial event A4 is a refractory event, and triggers an AFR interval (AFRI). Because the AFR interval has not expired prior to A5, A5 triggers a second AFR interval. Atrial event A6 occurs during PVARP and triggers an AFR interval. Because the AFR interval initiated by A6 has not expired prior to A7, A7 triggers another AFR interval. A8 does not trigger an AFRI. The atrial event A9 triggers an AFRI because it occurs during PVARP. A10 does not trigger and AFRI. The ventricle is paced after an AV delay. The AFR illustrated in FIG. 5B prevents the ICD from tracking fast atrial beats.

Figure 5C:
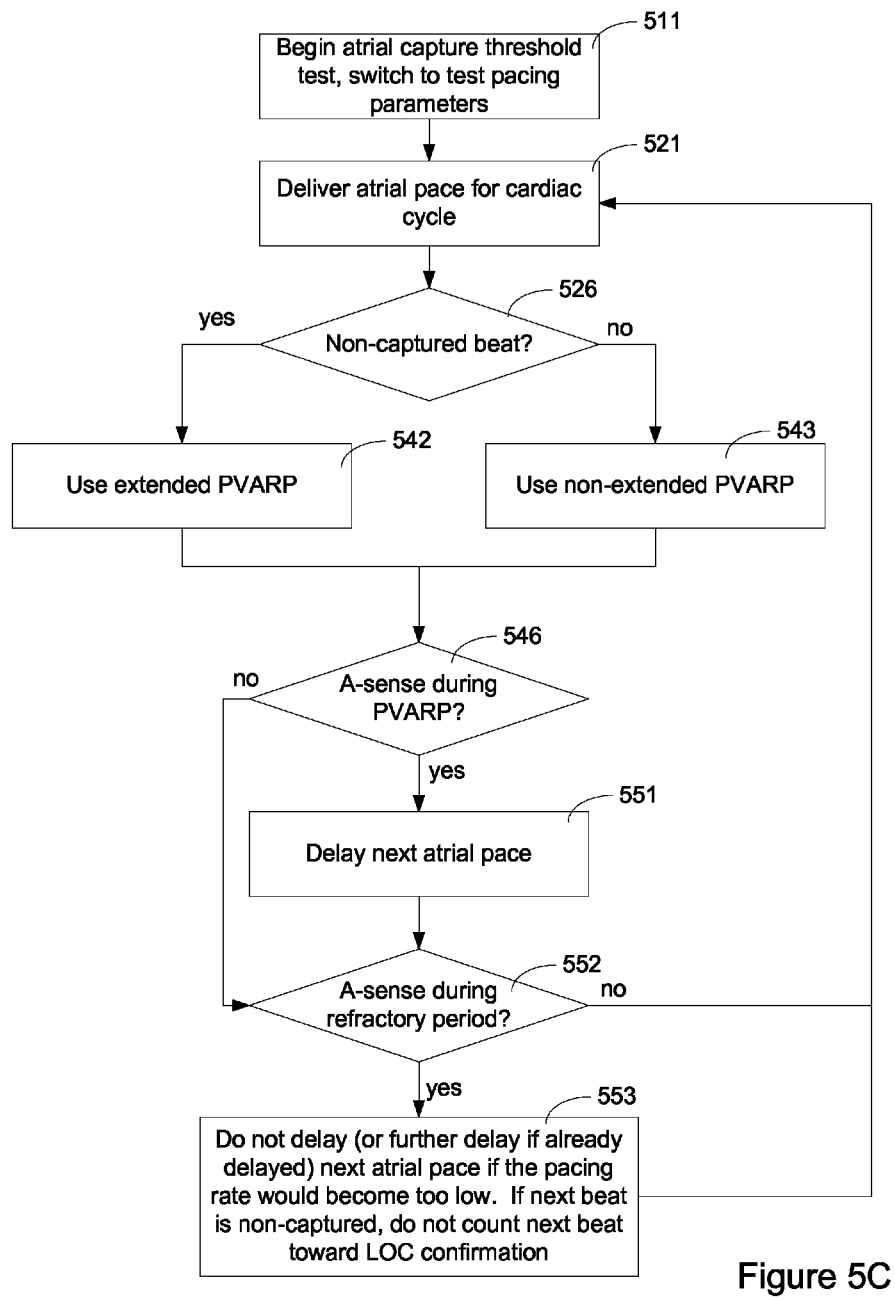
FIG. 5C is a flow diagram of a method for performing a capture threshold test when refractory periods in addition to PVARP are used during pacing.

FIG. 5C is a flow diagram of a method for performing a capture threshold test when refractory periods in addition to PVARP are used during pacing. The flow diagram of FIG. 5C illustrates the ICD response to a sensed atrial event that occurs within the non-PVARP refractory period, in this case the atrial flutter response interval, ATRI.

Before the step down portion of the atrial capture threshold test begins, threshold test parameters (e.g., pacing rate, pacing voltage, AV delay, etc.) are substituted 511 for the previous pacing parameters used during the normal pacing protocol. During the capture threshold test, atrial paces are delivered 521 for a number of cardiac cycles and the energy of the atrial paces is incrementally stepped down until loss of capture is confirmed. If a non-captured atrial beat is detected 526, the PVARP is extended 542 for the cardiac cycle. If the atrial beat is captured 526, then a normal (non-extended) PVARP is used 543. The ICD senses 546 for an atrial depolarization during the PVARP and delays 551 the next atrial pace if the atrial depolarization is detected during PVARP.

If no atrial depolarization is detected 546 during the PVARP, then the ICD checks to see if an atrial pace is sensed during a refractory period that extends beyond the PVARP, in this scenario, the ATRI. If so, the next atrial pace is not delayed 553 if delaying the atrial pace would cause the pacing rate to become too low. Because the next atrial pace is not delayed after a refractory atrial sense, the next atrial pace may occur during a time that the tissue is refractory, leading to a non-capture detection. This non-capture detection may be erroneous because the non-capture is due to tissue refractoriness rather than insufficient pacing energy. To account for this possible erroneous non-capture detection, the ICD does not count this possibly erroneous non-capture event towards the confirmation of loss of capture, e.g., x out of y non-captured beats or z non-captured beats at the same energy level for loss of capture confirmation.

In some embodiments, atrial backup pacing following a noncaptured atrial beat is used with or without a modified AV delay to avoid long-short cycles and mitigate the occurrence of arrhythmias during atrial capture threshold testing. Backup pacing following noncaptured paces ensures that the atrial tissue is refractory before a ventricular pace is delivered, thereby preventing retrograde conduction from the ventricular pace or intrinsic atrial depolarizations. In DDD pacing mode, back-up pacing may be used following a noncaptured atrial pace in conjunction with a modified AV interval and/or a modified PVARP during the cardiac cycle to reduce the likelihood of triggering arrhythmias. If an AAI pacing mode is implemented, back-up pacing may be used after a noncaptured atrial pace without AV interval and/or PVARP modifications.

Figure 6A:
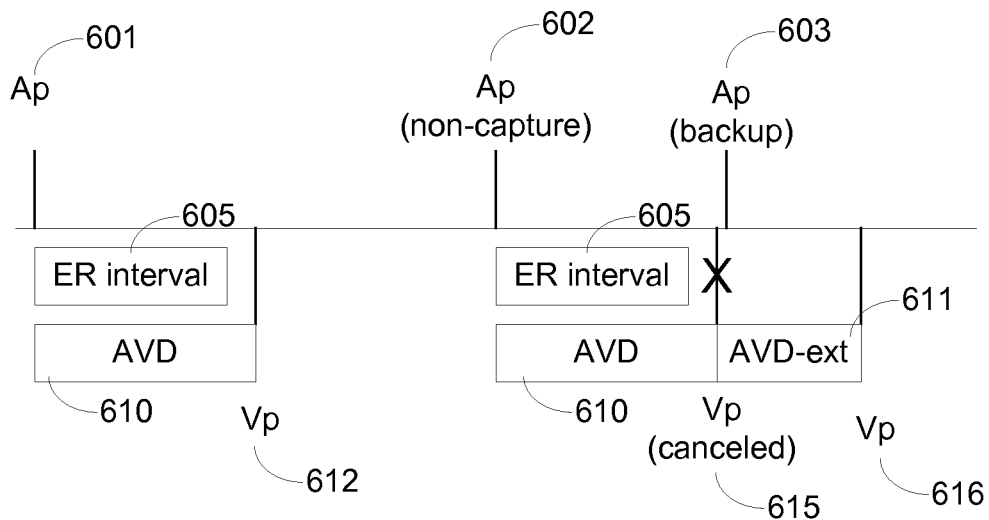
FIGS. 6A and 6B are timing diagrams that illustrate back up pacing used following a non-captured pace in atrial pacing and/or in atrial capture threshold testing in accordance with embodiments of the invention.
Figure 6B:
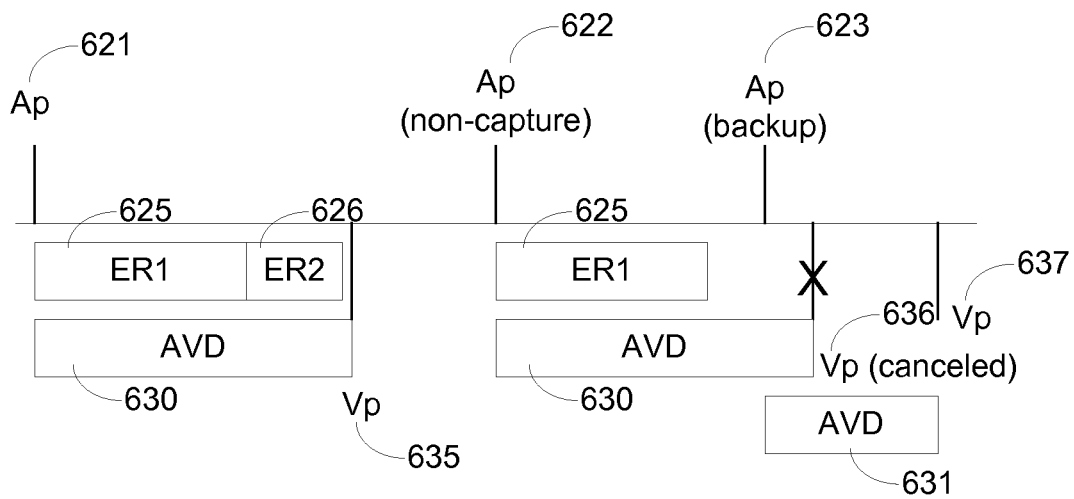

FIGS. 6A and 6B are pacing diagrams respectively illustrating backup pacing used in conjunction with a modified AV delay in accordance with embodiments of the invention. In FIG. 6A, one evoked response detection interval (ERI) 605 is used during each cardiac cycle following an atrial pace. An AV delay 610 that is slightly longer than the ER detection interval 605 is used. For example, if the ER detection interval 605 is about 80 ms, then the AV delay 610 can be set to about 90 ms. In the first cardiac cycle, an atrial pace 601 is delivered. A ventricular pacing pulse 612 for the cardiac cycle is scheduled to occur after the AV delay 610. The device evaluates the cardiac signal during the ER detection interval 605 and determines that the cardiac response to the atrial pace 601 is not noncapture, i.e., the cardiac response is a response other than noncapture. For example, the device may compare the cardiac signal that follows the pacing pulse to a threshold. If the cardiac signal does not achieve the threshold, then noncapture is detected. If the cardiac signal does achieve the threshold, then the device determines that a cardiac pacing response other than noncapture has occurred. In the latter case, the ventricular pace 612 is delivered after the AV delay 610 as scheduled.

On the next cardiac cycle, an atrial pace is delivered 602. A ventricular pacing pulse 615 is scheduled to occur after the AV delay 610. The device examines the cardiac signal during the ER interval 605 and determines that the atrial pace 602 did not capture the atrium. The device cancels the ventricular pace 615 and delivers an atrial backup pace 603 shortly after the end of the ER interval 605. The AV delay 610 is extended by an AVD-ext 611. After expiration of the AVD-ext 611, the ventricular pace 616 is delivered.

FIG. 6B illustrates an implementation that uses two ER detection intervals, ER-1 625 and ER-2 626 and optionally two AV delays 630, 631. In the first cycle, an atrial pace 621 is delivered, an AV delay 630 is initiated, and a ventricular pace 635 is scheduled to occur following the AV delay 630. The device analyzes the cardiac signal during the ER detection intervals 625, 626. For example, ER-1 625 may be set to about 50 ms which is long enough to detect noncapture and short enough to allow adjusting the AV delay which may be initially set to about 80 ms. In this cycle, noncapture of the atrial pace 621 is not detected during ER-1 625, and the device continues to analyze the cardiac signal during ER-2 626 to further identify the cardiac pacing response. The continued analysis allows the device to discriminate between cardiac responses other than non-capture, for example, to discriminate between capture, fusion, intrinsic activation or other possible cardiac pacing responses. No backup pace is delivered during this cycle; the ventricular pace 635 is delivered after the AV delay 630 as scheduled.

On the next cycle, the atrial pace 622 is delivered, an AV delay 630 is initiated, and a ventricular pace 636 is scheduled to occur following the AV delay 630. The device analyzes the cardiac signal during the ER-1 interval 625. For this cycle, at the end of ER-1, the device detects noncapture. The second ER detection interval 626 is canceled along with the ventricular pace 636. An atrial backup pace 623 is delivered and a second AV delay 631, e.g., about 60 ms, is initiated following the atrial backup pace 623. A ventricular pace 637 is delivered after the second AV delay 631.

Figure 7:
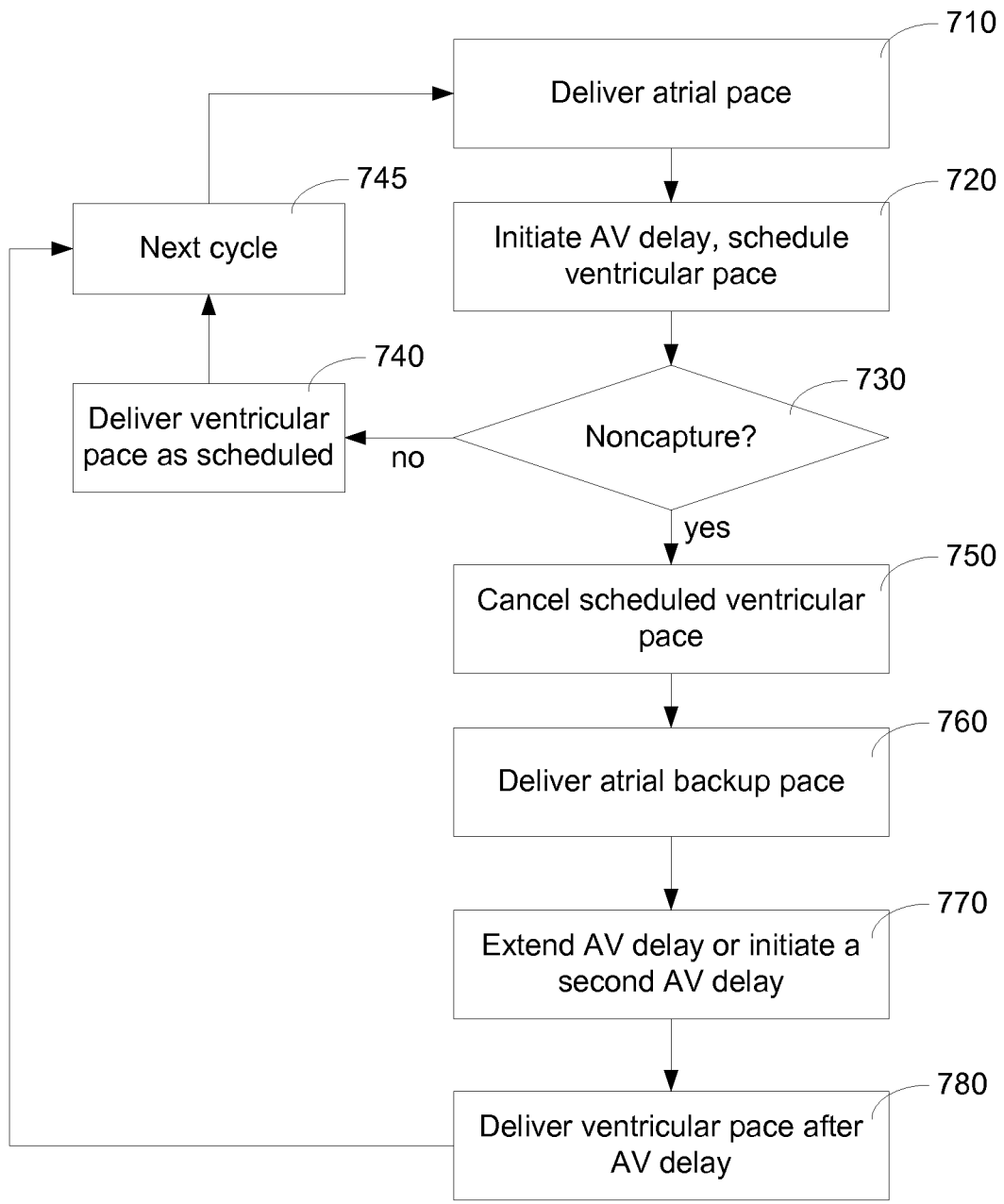
FIG. 7 is a flow diagram that illustrates a process of delivering backup pacing following a non-captured pace during atrial pacing and/or during atrial capture threshold testing using an extended or second AV delay in accordance with embodiments of the invention.

FIG. 7 is a flow diagram of a process that can be implemented in an implantable cardiac pacing device to produce pace timing similar to that illustrated in FIG. 6A. After delivery 710 of the atrial pace, an AV delay is initiated and a ventricular pace is scheduled 720. If the atrial pace is not noncaptured 730, then the ventricular pace is delivered 740 as scheduled and the next cycle 745 proceeds with another atrial pace 710.

However, if the atrial pace is noncaptured 730, then the scheduled ventricular pace is canceled 750, an atrial backup pace is delivered 760, and the AV delay is extended or a second AV delay is initiated 770. A ventricular pace is delivered 780 after the AV delay. The process continues in the next cycle 745.

Figure 8:
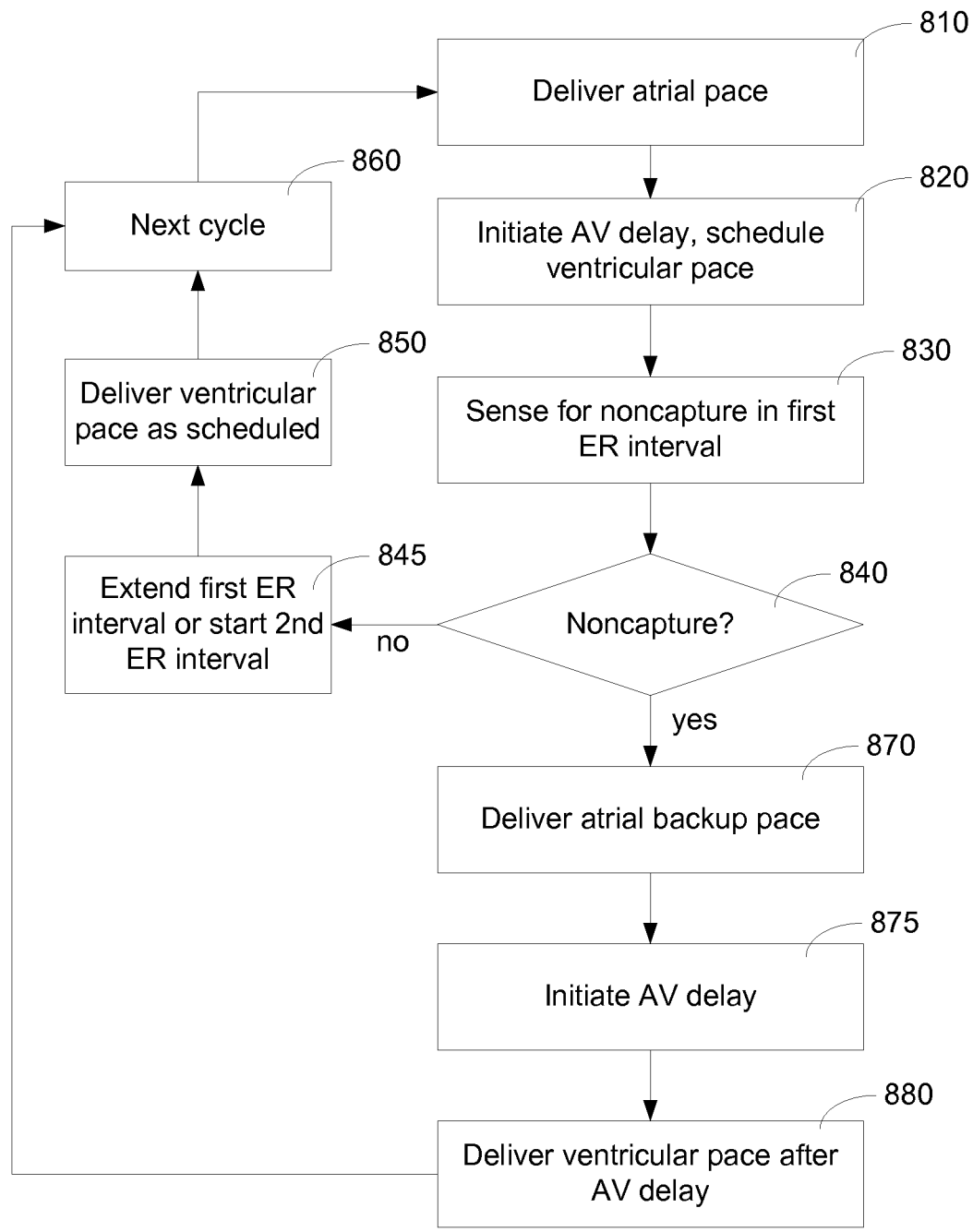
FIG. 8 is a flow diagram that illustrates the use of two evoked response intervals in accordance with embodiments of the invention.

FIG. 8 is a flow diagram of a process that produces pace timing similar that illustrated in FIG. 6B. After delivery 810 of the atrial pace, an AV delay is initiated and a ventricular pace is scheduled 820. The device senses 830 for atrial noncapture in the first ER interval. If noncapture is not detected 840, the initial ER interval is extended or a second ER interval is initiated 845 during which the device continues to analyze the cardiac signal to classify the pacing response. The ventricular pace is delivered 850 as scheduled and the process continues to the next cycle 860.

If noncapture is detected 840, an atrial backup pace is delivered 870. An AV delay is initiated 875 following the backup pace and the ventricular pace is delivered 880 after the AV delay. Following delivery of the ventricular pace, the process continues in the next cycle 860.

Figure 9:
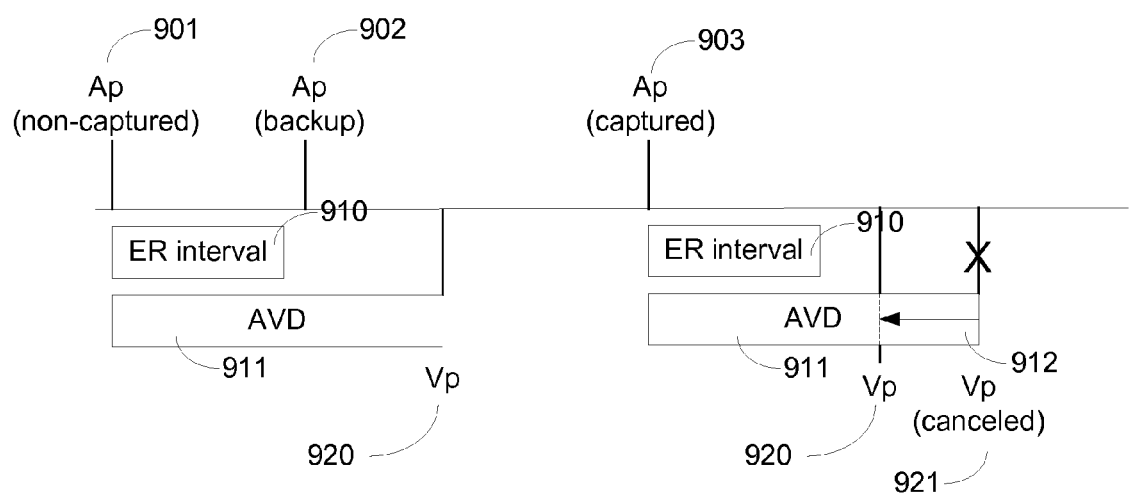
FIG. 9 is a timing diagram showing backup pace that is used in conjunction with a decrease in the AV delay in accordance with embodiments of the invention.

Yet another embodiment involves reducing an AV delay if a cardiac response other than noncapture is detected. The pacing timing diagram of FIG. 9 illustrates an atrial backup pacing approach. An atrial pace is delivered 901, an AV delay 911 is initiated following the atrial pace 901 and a ventricular pace 920 is scheduled. The device analyzes the cardiac signal following the atrial pace 901 in an ER interval 910. If noncapture is detected during the ER interval 910, an atrial backup pace 902 is delivered and the ventricular pacing pulse 920 is delivered as scheduled following the AV delay 911. Optionally, the initial AV delay 911 may not be used to time the ventricular pace 920, and an alternate AV delay, e.g., about 80 ms may be used instead.

On the next cardiac cycle, an atrial pace 903 is delivered, an AV delay 911 is initiated following the atrial pace 903 and a ventricular pace 921 is scheduled. The device analyzes the cardiac signal following the atrial pace 903 in an ER interval 910. If capture is detected, the AV delay 911 is reduced by an AV reduction amount 912. A ventricular pace 920 is delivered after reduced AV delay and the previously scheduled pace 921 is canceled. In one implementation, the initial AV delay 911 is about 140 ms and the AV delay reduction amount 912 is about 60 ms.

Figure 10:
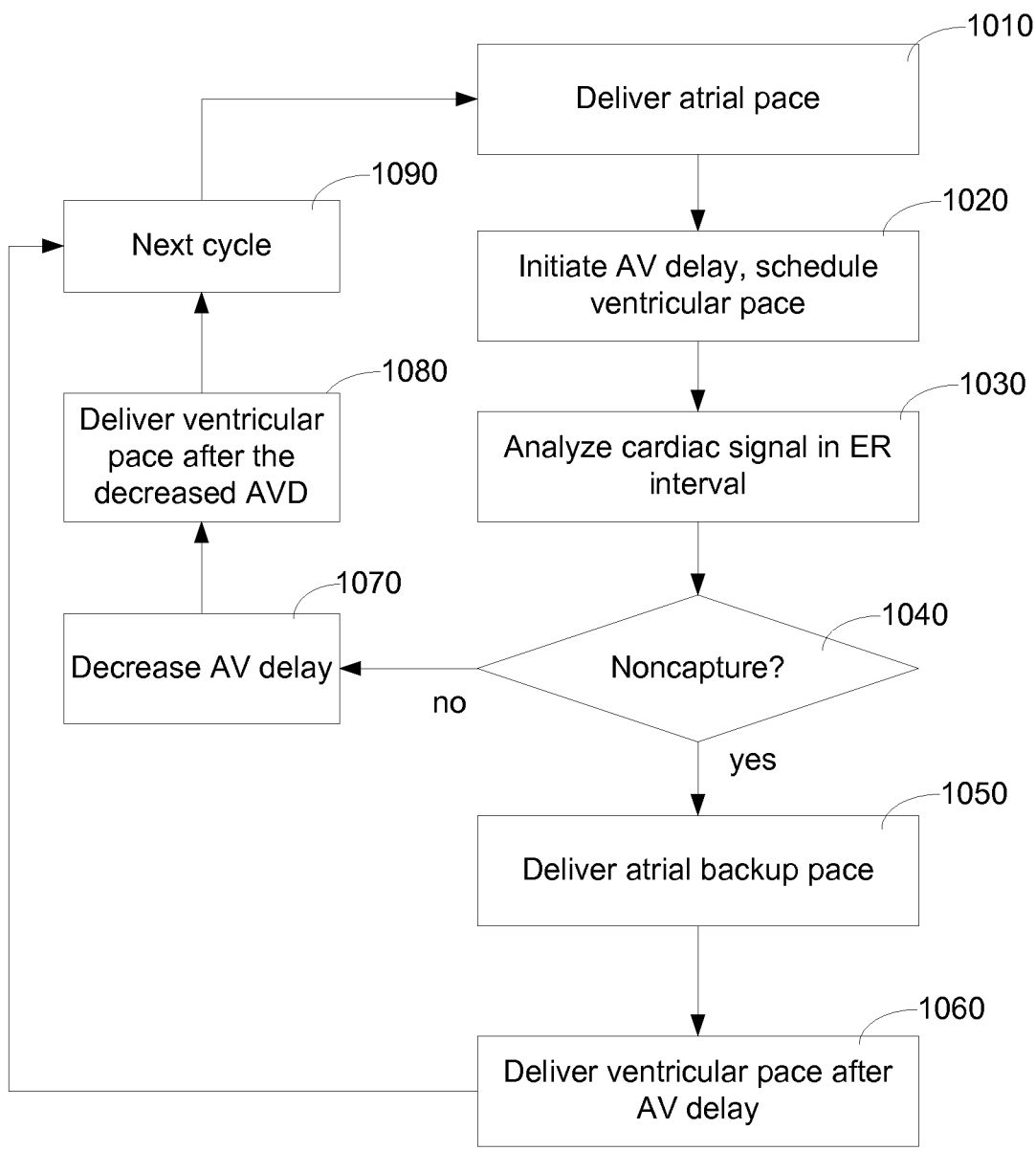
FIG. 10 is a flow diagram illustrating a process for delivering atrial backup pacing in accordance with embodiments of the invention.

FIG. 10 is a flow diagram of a process to produce pace timing similar to the diagram of FIG. 9. After delivery 1010 of the atrial pace, the device initiates an AV delay and schedules 1020 a ventricular pace. The cardiac signal following the pacing pulse is analyzed 1030 in an ER interval. If noncapture is detected 1040, then an atrial backup pace is delivered 1050 and the ventricular pace is delivered 1060 after the AV delay initiated in step 1020 and the process continues to the next cycle 1090. Optionally a different AV delay may initiated following the backup pace in which case the AV delay initiated in step 1020 would not be used to time the ventricular pace.

If noncapture is not detected, the AV delay initiated at step 1020 is decreased 1070 by a predetermined amount. The ventricular pacing pulse is delivered 1080 after the decreased AV delay and the process continues to the next cycle.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating an implantable cardiac rhythm device to deliver pacing to an atrium, the method, comprising:
   delivering atrial pacing during an atrial capture threshold test;
   using a post ventricular refractory period (PVARP) having a first PVARP duration during cardiac cycles of the atrial pacing in which an atrial pace captures the atrium;
   using an A-A interval having a first A-A interval duration between cardiac cycles of the atrial pacing in which the atrial pace captures the atrium; and
   using a PVARP having a second PVARP duration and using an A-A interval having a second A-A interval duration during cardiac cycles of the atrial pacing in which the atrial pace does not capture the atrium, wherein the second PVARP duration is greater than the first PVARP duration and the second A-A interval duration is greater than the first A-A interval duration and is extended from an atrial depolarization sensed during the PVARP having the second PVARP duration.

2. The method of claim 1, wherein the second PVARP duration is about 500 ms and the second A-A interval duration extends about 300 ms after an atrial depolarization sensed during the second PVARP duration.

3. The method of claim 1, wherein:
the atrial capture threshold test comprises a step-down capture threshold test; and
in response to a final noncaptured stepped down test pace, ending the atrial capture threshold test after the rate stabilization atrial pace.

4. The method of claim 3, wherein:
initiating the atrial capture threshold test comprises substituting a set of test pacing parameters in place of normal pacing parameters; and
ending the atrial capture threshold test comprises returning to the normal pacing parameters after delivery of the rate stabilization atrial pace.

5. The method of claim 4, wherein returning to the normal pacing parameters comprises returning to the normal pacing parameters on a next beat after the end of the atrial capture threshold test.

6. The method of claim 1, further comprising delivering a rate stabilization atrial pace after expiration of the A-A interval having the second A-A interval duration, the rate stabilization atrial pace initiating a next cardiac cycle and having an energy selected to produce capture of the atrium.

7. An implantable cardiac therapy device, comprising:
electrodes configured to be electrically coupled to an atrium;
a pulse generator configured to deliver atrial pacing pulses to the atrium;
a cardiac response classification processor configured to discriminate noncaptured responses to the atrial pacing pulses from other cardiac responses to the atrial pacing pulses; and
a pacing control module configured to control delivery of the pacing pulses and timing intervals used during pacing cycles during an atrial capture threshold test, the pacing control module configured to use a post ventricular refractory period (PVARP) having a first duration during cardiac cycles in which an atrial pace captures the atrium, to use an A-A interval having a first A-A interval duration between cardiac cycles during cardiac cycles in which the atrial pace captures the atrium, and to use a PVARP having a second PVARP duration and an A-A interval having a second A-A interval duration during cardiac cycles in which the atrial pace does not capture the atrium, wherein the second PVARP duration is greater than the first PVARP duration and the second A-A interval duration is greater than the first A-A interval duration and is extended from an atrial depolarization sensed during the PVARP having the second PVARP duration.

8. The device of claim 7, wherein:
the second PVARP duration is about 500 ms; and
the second A-A interval duration extends about 300 ms from an atrial depolarization sensed during the PVARP.

9. The device of claim 7, wherein:
the pacing control module includes a capture threshold module configured to control test paces delivered during a step-down atrial capture threshold test; and
in response to a final noncaptured stepped down test pace, the capture threshold test module is configured to end the capture threshold test after the rate stabilization atrial pace.

10. The device of claim 9, wherein:
the capture threshold test module is configured to substitute a set of test pacing parameters during the capture threshold test in place of normal pacing parameters and to return to the normal pacing parameters after delivery of the rate stabilization atrial pace.

11. The device of claim 7, wherein the pacing control module is configured to deliver a rate stabilization atrial pace after expiration of the second A-A interval duration, the rate stabilization atrial pace initiating a next cardiac cycle and having an energy selected to produce capture of the atrium.

12. A method of operating an implantable cardiac rhythm device to deliver pacing to an atrium, the method, comprising:
delivering atrial pacing;
using a post ventricular refractory period (PVARP) having a first PVARP duration during cardiac cycles of the atrial pacing in which an atrial pace captures the atrium;
using an A-A interval having a first A-A interval duration between cardiac cycles of the atrial pacing in which the atrial pace captures the atrium;
using a PVARP having a second PVARP duration and using an A-A interval having a second A-A interval duration during cardiac cycles of the atrial pacing in which the atrial pace does not capture the atrium, wherein the second PVARP duration is greater than the first PVARP duration and the second A-A interval duration is greater than the first A-A interval duration and is extended from an atrial depolarization sensed during the PVARP having the second PVARP duration; and
delivering a rate stabilization atrial pace after expiration of the A-A interval having the second A-A interval duration, the rate stabilization atrial pace initiating a next cardiac cycle and having an energy selected to produce capture of the atrium.

* * * * *